United States Patent [19]

Clark et al.

[11] Patent Number: 5,237,087
[45] Date of Patent: Aug. 17, 1993

[54] PROCESS FOR THE PREPARATION OF CHLORINATED AND FLUORINATED BENZENE COMPOUNDS BY SELECTIVE NUCLEOPHILIC FLUORODENITRATION

[75] Inventors: James H. Clark, York, Great Britain; Andrew J. Beaumont, Morland Penrith, South Africa; Nubia Boechat, Rio De Janeiro, Brazil

[73] Assignee: Hoechst Aktiengesellschaft, Frankfurt, Fed. Rep. of Germany

[21] Appl. No.: 949,031

[22] Filed: Sep. 21, 1992

[30] Foreign Application Priority Data

Sep. 21, 1991 [EP] European Pat. Off. ........... 91116092

[51] Int. Cl.$^5$ ................ C07C 253/30; C07C 255/50; C07C 67/307
[52] U.S. Cl. ................................. 558/425; 560/111
[58] Field of Search ......................... 558/425; 560/111

[56] References Cited

U.S. PATENT DOCUMENTS

| | | | |
|---|---|---|---|
| 3,764,617 | 10/1973 | Heckert et al. | 560/111 X |
| 4,229,365 | 10/1980 | Oeser et al. | 558/425 |
| 4,590,315 | 5/1986 | Maul et al. | 558/425 X |
| 4,978,769 | 12/1990 | Kysela et al. | 558/423 |

FOREIGN PATENT DOCUMENTS 0296479 12/1988 European Pat. Off. .
0354444 2/1990 European Pat. Off. .

OTHER PUBLICATIONS

Clark, J. H. et al, *Tetrahedron Letters* 26: pp. 2233–2236, (1985).
Jilek, J., et al, *Chem. Abs.* 109:170051d, p. 682, (1988).
Jilek, J., et al. *Chem. Abs.* 109:230547g, p. 814, (1988).

Soundararajan, N., et al, *J. Org. Chem.* 55: pp. 2034–2044, (1990).

*Primary Examiner*—Joseph Paul Brust
*Attorney, Agent, or Firm*—Connolly & Hutz

[57] ABSTRACT

A process for the preparation of chlorinated and fluorinated benzene compounds of the general formula (1)

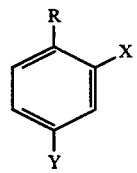

in which R denotes —CN or —COOalkyl($C_1$–$C_6$), and X and Y each denote chlorine or fluorine, X and Y being not identical, by fluorodenitration, which comprises reacting a compound of the formula (2)

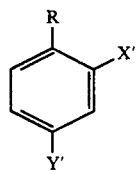

in which R is defined as above, and X' and Y' each denote chlorine or nitro, X' and Y' being nor identical, with potassium fluoride in a dipolar aprotic solvent in the presence of a transfer catalyst at a temperature from about 50° C. to about 250° C.

14 Claims, No Drawings

PROCESS FOR THE PREPARATION OF CHLORINATED AND FLUORINATED BENZENE COMPOUNDS BY SELECTIVE NUCLEOPHILIC FLUORODENITRATION

The present invention relates to a process for the preparation of chlorinated and fluorinated benzene compounds of the general formula (1) indicated below by selective nucleophilic fluorodenitration. These compounds represent intermediates for the preparation of pharmaceuticals and plant protective agents.

Many processes are known for the fluorination of aromatic compounds of which the direct exchange of fluorine for chlorine and the indirect exchange of fluorine for nitro are the best known and most widely applied in industry. The latter method requires the initial reduction of the nitro compound followed by the preparation of a diazonium intermediate which is in turn decomposed to the fluoroaromatic compound. The methodology suffers from being multistep and involving potentially explosive intermediates. The direct exchange of fluorine for chlorine ("halex") is more straightforward but can suffer from low selectivity in the case of multisubstituted aromatic compounds and generally from the need for ring activation to make the chlorine labile.

Little useful selectivity can be expected in the fluorination of 2,4-dichloroaromatic compounds since a —M group such as $NO_2$ is required in the p-position to provide the necessary activation and this will act to make both chlorines labile to nucleophilic attack by fluoride.

In Czech CS 246,346 (Chem. Abs. 1988, 109, 170051d) there is described the synthesis of 4-fluoro-2-nitrobenzonitrile (an intermediate for antipsychotics and narcoleptics) starting from 4-fluoro-2-nitroaniline using diazotisation and cyanation. In Czech CS 246,347 (Chem. Abs. 1988, 109, 230547g) there is described the acid hydrolysis of this nitrile to the corresponding benzoic acid. Alternatively, the acid has been prepared by nitric acid oxidation of the corresponding toluene as described in J. Org. Chem., 1990, 55, 2034.

Fluorodenitration has been put forward as an alternative to halex as a one-step method for the selective nucleophilic fluorination of aromatic substrates. This method has been described in a number of articles including TETRAHEDRON LETTERS, 1985, 2233.

Generally the nitro group is considered to be a better leaving group than the chlorine atom, especially when it is not in conjugation with the ring.

There has now surprisingly been found a process for the preparation of chlorinated and fluorinated benzene compounds of the general formula (1)

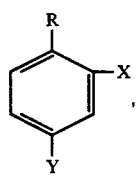

(1)

in which R denotes —CN or —COOalkyl($C_1$-$C_6$), and X and Y each denote chlorine or fluorine, X and Y being however not identical, by fluorodenitration, which comprises reacting a compound of the formula (2)

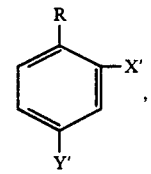

(2)

in which R is defined as above, and X' and Y' each denote chlorine or nitro, X' and Y' being however not identical, with potassium fluoride in a dipolar aprotic solvent in the presence of a phase transfer catalyst at a temperature from about 50° C. to about 250° C., preferably from about 100° to about 200° C.

Suitable aprotic solvents are, for instance, dimethylformamide, N,N-dimethylacetamide, dimethylsulphone, dimethylsulphoxide, tetramethylenesulphone (sulpholane), tetramethylenesulphoxide, diphenylsulphone, diphenylsulphoxide, N-methylpyrrolidone or 1,3-dimethylimidazoline-2-one.

Suitable phase transfer catalysts are, for instance, tetraalkyl($C_1$-$C_{18}$)-ammonium halides, such as the chlorides or bromides, tetraalkyl($C_1$-$C_{18}$)-phosphonium halides, such as the chlorides or bromides, tetraphenylphosphonium halides, such as the chlorides or bromides, [(phenyl)$_m$(alkyl($C_1$-$C_{18}$))$_n$]-phosphonium halides, such as the chlorides or bromides, m being 1-3, n being 3-1, and m+n being 4. Preferred phase transfer catalysts are tetramethylammonium chloride or -bromide and tetraphenylphosphoniumchloride or -bromide.

The mole ratio of the potassium fluoride to the aromatic starting compound of the said formula (2) is about 5:1 to about 1:1, preferably about 3:1 to about 1,1:1.

The mole ratio of the aromatic starting compound of the said formula (2) to the phase transfer catalyst is about 20:1 to about 1:1, preferably about 10:1 to about 5:1.

With respect to the reaction temperature the preferred temperature is dependent on the aprotic solvent used. For instance, for the most preferred dipolar aprotic solvent employed in the inventive process, dimethylsulphoxide, the convenient reaction temperature range is from about 50° to about 150° C., preferably from about 100° to about 130° C., the optimum reaction temperature being about 130° C. For tetramethylenesulphone (sulpholane) the preferred temperature range is from about 160° C. to about 200° C. If there are employed lower temperatures, there are achieved unacceptably low rates of reaction, whereas higher temperatures give increasing amounts of by-products, especially in the case of the starting compound of the formula (3)

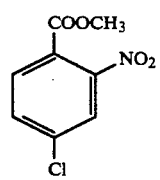

(3)

Reaction times can be varied to optimize product formation under the conditions employed, but for the best conditions is typically a reaction time in the range from about 20 to about 30 hours for the aromatic starting compounds (formula 2) with R=—COOalkyl(-

$C_1$–$C_6$), and less than 2 hours for the starting compounds with R=—CN.

Table 1 gives results from a series of experiments with one starting compound of the afore-said formula (3) under different conditions. Table 2 gives the best results obtained for all four starting compounds under the most preferred conditions of potassium fluoride, starting compound and tetraphenylphosphonium bromide (mole ratio 2:1:0.2) in dimethylsulphoxide.

The instant process can be carried out at atmospheric pressure as well as at a lower pressure (vacuo) or at an elevated pressure (superatmospheric pressure).

EXAMPLE 1

Anhydrous potassium fluoride (11.6 g, 0.2 mole, dried at 300° C.), 4-chloro-2-nitromethylbenzoate (21.5 g, 0.1 mole) and tetraphenylphosphonium bromide (8.4 g, 0.02 mole) were vigorously stirred together at 130° C. in pre-distilled dimethylsulphoxide. After 26 h, g.c. showed a conversion of the substrate to 4-chloro-2-fluoromethylbenzoate of 72% along with trace amounts (<2%) of the fluoronitro and difluoro products and a small amount (2%) of 3-chloronitrobenzene. After aqueous washing the organic residue was sublimed to give a 46% yield of the pure 4-chloro-2-fluoromethyl-benzoate product. The product, isolated as a solid, showed the following data:

(i) Mass spectra: m/z 190 188 (parent), 159, 157 (major peak), 131, 129, 109, 94, 93 and 74. [exact mass 188.0044 (found); calculated 188.0040].

(ii) Infrared (KBr-disc): 1730, 1212, 1315, 760 and 899 $cm^{-1}$.

(iii) $^1$H-NMR (high resolution in $CDCl_3$): 7.90 (dd, 1H, J=8 and 9 Hz), 7.18 (mult, 2H) and 3.94 ppm (s, 3H).

(iv) $^{19}$F-NMR (high resolution in $CDCl_3/CFCl_3$): −107.12 ppm (mult).

(v) $^{13}$C-NMR (high resolution in $CDCl_3$): 167.62, 164.05, 140.10, 133.00, 124.44, 117.43, 117.43, 117.13, 52.39 ppm.

All above data are consistent with the structure.

EXAMPLE 2

Using the same conditions as in Example 1,2-chloro-4-nitromethylbenzoate reacted to give 2-chloro-4-fluoromethylbenzoate in 60% yield by g.c. after 24 h. Separation of the organic products on an alumina column gave 35% of pure 2-chloro-4-fluoromethylbenzoate. This product showed the following data:

(i) Mass spectra: m/z 190, 188 (parent), 159, 157 (major peak), 129, 109, 94, 93, 74 and 69. [exat mass 188.0028 (found); calculated 188.0040].

(ii) Infrared (film): 1737, 1245, 1280, 760 and 899 $cm^{-1}$.

(iii) $^1$H-NMR (high resolution in $CDCl_3$): 7.91 (dd, 1H, J=6 and 9 Hz), 7.19 (dd, 1H, J=2 and 8 Hz), 7.03 (mult., 1H) and 3.94 ppm (s, 3H).

(iv) $^{19}$F-NMR (high resolution in $CDCl_3/CFCl_3$): −105.90 ppm with respect to $CFCl_3$ (mult).

(v) $^{13}$C-NMR (high resolution in $CDCl_3$): 168.75, 163.98, 134.94, 132.67, 125.08, 116.96, 113.44, 51.35 ppm.

All above data are consistent with the structure.

EXAMPLE 3

Using the same conditions as in Example 1,2-chloro-4-nitrobenzonitrile reacted to give 2-chloro-4-fluorobenzonitrile in 95% yields by g.c. after 1.5 h. The product, isolated as a solid, showed the following data:

(i) Melting point: 62°–65° C.

(ii) Mass spectra: m/z 157, 155 (parent and major peak), 120, 100, 94, 93, 75, 50.

(iii) $^{19}$F-NMR ($CDCl_3/CFCl_3$): −100.62 (mult).

(iv) $^{13}$C-NMR ($CDCl_3$): 206.5 (s), 166.3 (d, J=230.7 Hz), 138.8 (d, J=11 Hz), 137.3 (d, J=11 Hz), 117.6 (d, J=25.6 Hz), 116.5 (d, J=21.9 Hz), 106.8 ppm (s).

All above data are consistent with the structure.

EXAMPLE 4

Using the same conditions as in Example 1,4-chloro-2-nitrobenzonitrile reacted to give 4-chloro-2-fluorobenzonitrile in 95% yields by g.c. after 0.5 h. The product, isolated as a solid, showed the following data:

(i) Melting point: 66°–74° C.

(ii) Mass spectra: m/z 157, 155 (parent and major peak) 120, 100, 93, 75, 73, 50.

(iii) $^{19}$F-NMR ($CdCl_3/CFCl_3$): −104.34 ppm (mult).

(iv) $^{13}$C-NMR ($CDCl_3$): 206.7 (s), 165.5 (d, J=181.9 Hz), 141.3 (d, J=9.8 Hz), 134.2 (s), 126.8 (d, J=3.7 Hz), 118.2 (d, J=23.2 Hz), 100.9 ppm (d, J=14.6 Hz).

All above data are consistent with the structure.

EXAMPLE 5

2-Chloro-4-nitrobenzonitrile was reacted under the same conditions as described in Example 1, using however instead of 0.02 mole tetraphenylphosphonium bromide the equimolar amount of tetramethylammoniumchloride. After 1.5 h, g.c. showed a conversion of the 2-chloro-4-nitrobenzonitrile to 2-chloro-4-fluorobenzonitrile of 90%. The product, isolated as a solid, showed the data as indicated in Example 3.

EXAMPLE 6

4-Chloro-2-nitrobenzonitrile was reacted under the same conditions as described in Example 1, using however instead of 0.02 mole tetraphenylphosphonium chloride the equimolar amount of tetramethylammonium chloride. After 1.5 h, g.c. showed a conversion of the 4-chloro-2-nitrobenzonitrile to 4-chloro-2-fluorobenzonitrile of 93%. The product, isolated as a solid, showed the data as indicated in Example 4.

TABLE 1

The Fluorodenitration of 4-Chloro-2-Nitromethylbenzoate under different reaction conditions

| Mole ratio starting compound: KF:Ph4PBr | Solvent/ Temp. (°C.)/ Time (h) | CO2Me / NO2 / Cl | CO2Me / F / Cl | CO2Me / NO2 / F | CO2Me / F / F | NO2 / Cl | CO2Me / OMe / Cl | CO2Me / NO2 / OMe |
|---|---|---|---|---|---|---|---|---|
| 1:4:0 | Sulpholane/ | — | 30 | — | — | 63 | 2 | 1.3 |
| 1:4:0.1 | 220/0.5 | — | 27 | — | — | 66 | 3 | 2 |

TABLE 1-continued

The Fluorodenitration of 4-Chloro-2-Nitromethylbenzoate under different reaction conditions

| Mole ratio starting compound: KF:Ph₄PBr | Solvent/ Temp. (°C)/ Time (h) | CO₂Me, NO₂, Cl | CO₂Me, F, Cl | CO₂Me, NO₂, F | CO₂Me, F, F | NO₂, Cl | CO₂Me, OMe, Cl | CO₂Me, NO₂, OMe |
|---|---|---|---|---|---|---|---|---|
| 1:4:0.1 | Sulpholane/ 180/0.5 | 14 | 45 | 1.3 | — | 38 | — | — |
| 1:4:0.1 | Dimethyl-acetamide/ 130/25 | 62 | 31 | 5 | — | 2 | — | — |
| 1:4:0.1 | Dimethyl-sulphoxide/ 130/26 | 39 | 57 | 1.8 | 0.4 | 1.8 | — | — |
| 1:4:0.2 | | 23 | 72 | 0.9 | — | 2.5 | — | — |
| 1:4:0.3 | | 22 | 72 | 1 | 1 | 3 | — | — |
| 1:2:0.1 | | 28 | 65 | 0.8 | 0.8 | 4 | — | — |
| 1:2:0.2 | | 33 | 62 | 1.3 | 0.6 | 2 | — | — |
| 1:2:0.3 | | 18 | 73 | 0.8 | 1.7 | 5 | — | — |
| 1:2:0.4 | | 17 | 72 | 0.8 | 1 | 7 | — | — |

TABLE 2

The Fluorodenitration of starting compounds under optimum conditions
(KF(2.0)/starting compound (1.0)/Ph₄PBr (0.2)/dimethylsulphoxide/130° C.)

| Starting compound | Reaction Time/h | Product | G.c. Yield % | Isolated Yield % |
|---|---|---|---|---|
| CO₂Me, NO₂, Cl | 27 | CO₂Me, F, Cl | 72 | 46 |
| CO₂Me, Cl, NO₂ | 24 | CO₂Me, Cl, F | 60 | 35 |
| CN, NO₂, Cl | 0.5 | CN, F, Cl | 95 | 68 |
| CN, Cl, NO₂ | 1.5 | CN, Cl, F | 95 | 70 |

We claim:

1. A process for the preparation of chlorinated and fluorinated benezene compounds of the general formula (1)

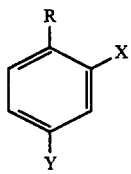

in which R denotes —CN or —COOalkyl($C_1$–$C_6$) and X and Y each denote chlorine or fluorine, X and Y being not identical, by fluorodenitration, which comprises reacting a compound of the formula (2)

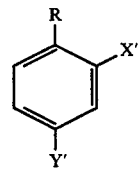

in which R is defined as above, and X' and Y' each denote chlorine or nitro, X' and Y' being not identical, with potassium fluoride in a dipolar aprotic solvent in the presence of a phase transfer catalyst at a temperature from about 50° C. to about 250° C.

2. The process as claimed in claim 1, wherein the fluorodenitration is performed at a temperature from about 100° to about 200° C.

3. The process as claimed in claim 1, wherein the fluorodenitration is performed in dimethylformamide, N,N-dimethylacetamide, dimethylsulphone, dimethylsulphoxide, tetramethylenesulphone, tetramethylenesulphoxide, diphenylsulphone, diphenylsulphoxide, N-methylpyrrolidone or 1,3-dimethylimidazoline-2-one as dipolar aprotic solvent.

4. The process as claimed in claim 1, wherein the fluorodenitration is performed in tetramethylenesulphone at a temperature from about 160° C. to about 200° C.

5. The process as claimed in claim 1, wherein the fluorodenitration is performed in dimethylsulphoxide at a temperature from about 50° to about 150° C.

6. The process as claimed in claim 1, wherein the fluorodenitration is performed in dimethylsulphoxide at a temperature from about 100° to about 130° C.

7. The process as claimed in claim 1, wherein the fluorodenitration is performed in N,N-dimethylacetamide at about 130° C.

8. The process as claimed in claim 1, wherein the fluorodenitration is performed in the presence of tetraalkyl($C_1$–$C_{18}$)-ammonium chlorides or -bromides, tetraalkyl($C_1$–$C_{18}$)-phosphonium chlorides or -bromides, tetraphenylphosphonium chloride or -bromide, [(phenyl)$_m$(alkyl-($C_1$–$C_{18}$))$_n$]-phosphonium chlorides or -bromides, m being 1–3, n=3–1 and m+n=4.

9. The process as claimed in claim 1, wherein the fluorodenitration is performed in the presence of tetraphenylphosphonium bromide.

10. The process as claimed in claim 1, wherein the mole ratio of the aromatic starting compound to the phase transfer catalyst is about 20:1 to about 1:1.

11. The process as claimed in claim 1, wherein the mole ratio of the aromatic starting compound to the phase transfer catalyst is about 10:1 to about 5:1.

12. The process as claimed in claim 1, wherein the mole ratio of the potassium fluoride to the aromatic starting compound is about 5:1 to about 1:1.

13. The process as claimed in claim 1, wherein the mole ratio of the potassium fluoride to the aromatic starting compound is about 3:1 to about 1.1:1.

14. the process as claimed in claim 1, wherein the fluorodenitration is performed at atmospheric pressure or at a lower or elevated pressure.

* * * * *